(12) United States Patent
Omernick et al.

(10) Patent No.: US 8,243,883 B2
(45) Date of Patent: Aug. 14, 2012

(54) WIRELESS X-RAY DETECTOR OPERATION COORDINATION SYSTEM AND METHOD

(75) Inventors: Jon Charles Omernick, Wauwatosa, WI (US); Manfred David Boehm, Waukesha, WI (US); Gireesha C. Rao, Pewaukee, WI (US); James Zhengshe Liu, Glenview, IL (US); Chuande Liu, Waukesha, WI (US); Kiran Shankaranarayana, Bangalore (IN); Karla Angelica Arista, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 280 days.

(21) Appl. No.: 12/776,207

(22) Filed: May 7, 2010

(65) Prior Publication Data

US 2011/0274251 A1    Nov. 10, 2011

(51) Int. Cl.
*H05G 1/64* (2006.01)
(52) U.S. Cl. .......................... 378/116; 378/98
(58) Field of Classification Search .................... 378/98, 378/98.8, 114–116
See application file for complete search history.

(56) References Cited

U.S. PATENT DOCUMENTS

2007/0116180 A1   5/2007   Omernick et al.
2009/0118606 A1   5/2009   Jabri et al.
2009/0130983 A1   5/2009   Venturino et al.

OTHER PUBLICATIONS

U.S. Appl. No. 12/506,067, filed Jul. 20, 2009, Sabol et al.

*Primary Examiner* — Courtney Thomas
(74) *Attorney, Agent, or Firm* — Fletcher Yoder, P.C.

(57) ABSTRACT

In one embodiment, a method for coordinating operation of X-ray detectors in a wireless X-ray system includes detecting multiple wireless X-ray detectors within an operative range of an X-ray base station, the detected X-ray detectors each having one of multiple possible statuses, including an active status corresponding to a designation of the X-ray detector as a desired recipient of radiation during a current X-ray imaging sequence, an inactive status corresponding to a designation of the X-ray detector as not the desired recipient of radiation during a current X-ray imaging sequence, and an unenabled status corresponding to the X-ray detector not being configured to operate with the X-ray base station. The method also includes determining the current status of each detected X-ray detector and displaying on a user-viewable screen a visual indication of the status of each detected X-ray detector.

32 Claims, 7 Drawing Sheets

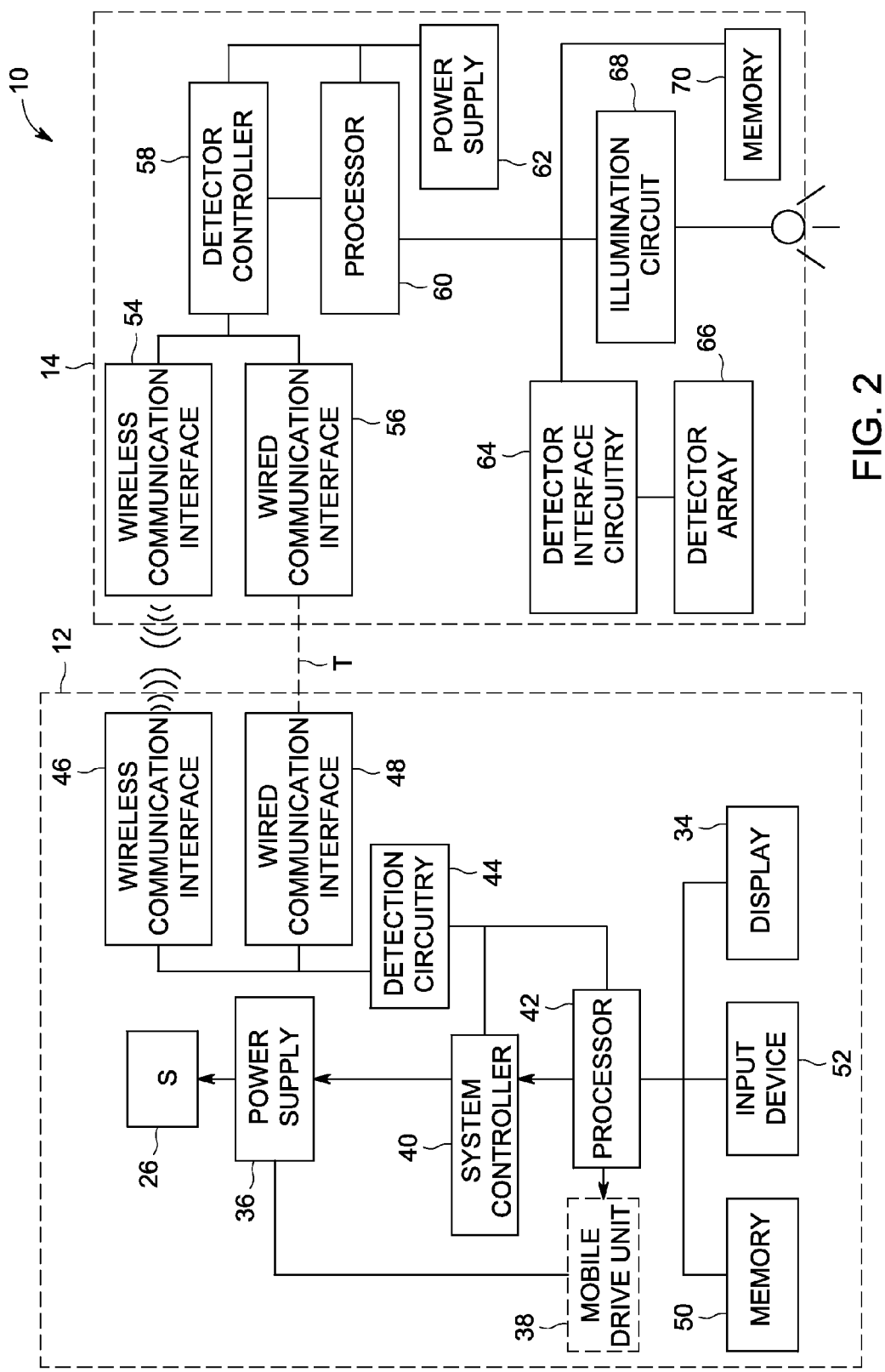

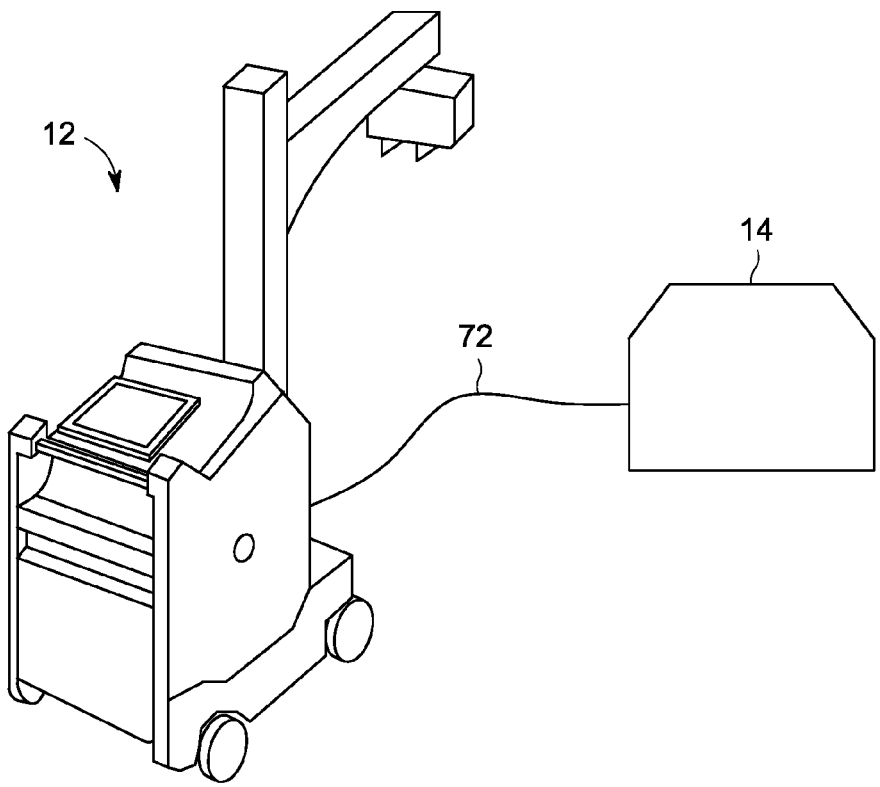

US 8,243,883 B2

WIRELESS X-RAY DETECTOR OPERATION COORDINATION SYSTEM AND METHOD

BACKGROUND OF THE INVENTION

The subject matter disclosed herein relates to X-ray imaging systems and more particularly to X-ray imaging systems using wireless digital detectors.

The advent of digital X-ray detectors has brought enhanced workflow and high image quality to medical imaging. In the current state of the art medical imaging environments, X-ray imaging systems include an imaging subsystem and a detector. The imaging subsystem may be fixed or mobile and may use a detachable or wireless detector. Current imaging subsystems are calibrated for and permanently integrated with specific detectors, potentially multiple wireless detectors. That is, any one of several detectors may function with the imaging subsystem to receive radiation during an imaging sequence and produce image data that can be reconstructed into the desired image. However, if the imaging system lacks the ability to sense and manage multiple wireless detectors, potential problems may arise. For example, a user may have trouble determining prior to an exposure whether the specific detector being used is configured with the imaging system. Also, if multiple detectors configured with the imaging system are located within the vicinity of the imaging system, exposures may occur with a detector that is not the primary detector. This may pose problems in the retrieval of the image data, and in come cases, could require reimaging the subject, raising the level of exposure unnecessarily.

BRIEF DESCRIPTION OF THE INVENTION

In accordance with one embodiment, a method for coordinating operation of X-ray detectors in a wireless X-ray system includes detecting multiple wireless X-ray detectors within an operative range of an X-ray base station, a first of the X-ray detector having an active status corresponding to a designation of the first X-ray detector as a desired recipient of radiation during a current X-ray imaging sequence, and a second X-ray detector having a status different from the active status. The method also includes determining the current status of each detected X-ray detector and displaying on a user-viewable screen a visual indication of the status of each detected X-ray detector.

In accordance with another embodiment, a method for coordinating operation of X-ray detectors in a wireless X-ray system includes detecting multiple wireless X-ray detectors within an operative range of an X-ray base station, the detected X-ray detectors each having one of multiple possible statuses, including an active status corresponding to a designation of the X-ray detector as a desired recipient of radiation during a current X-ray imaging sequence, an inactive status corresponding to a designation of the X-ray detector as not the desired recipient of radiation during a current X-ray imaging sequence, and an unenabled status corresponding to the X-ray detector not being configured to operate with the X-ray base station. The method also includes determining the current status of each detected X-ray detector and displaying on a user-viewable screen a visual indication of the status of each detected X-ray detector.

In accordance with a further embodiment, a wireless X-ray detector operation coordination system includes detection circuitry configured to detect a plurality of wireless X-ray detectors within an operative range of an X-ray base station and to determine a current status of each detected X-ray detector, the detected X-ray detectors each having one of multiple possible statuses, including an active status corresponding to a designation of the X-ray detector as not the desired recipient of radiation during a current X-ray imaging sequence, and an unenabled status corresponding to the X-ray detector not being configured to operate with the X-ray base station. The system also includes a user-viewable screen configured to display a visual indication of the status of each detected X-ray detector.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 2 is a diagrammatical overview of the wireless X-ray system of FIG. 1;

FIG. 3 is a perspective view of a detector connected to an X-ray base station of FIG. 1, in accordance with aspects of the present technique;

FIG. 4 is an example of a screen for registering the detector with the wireless X-ray system;

DETAILED DESCRIPTION OF THE INVENTION

Figure 1:
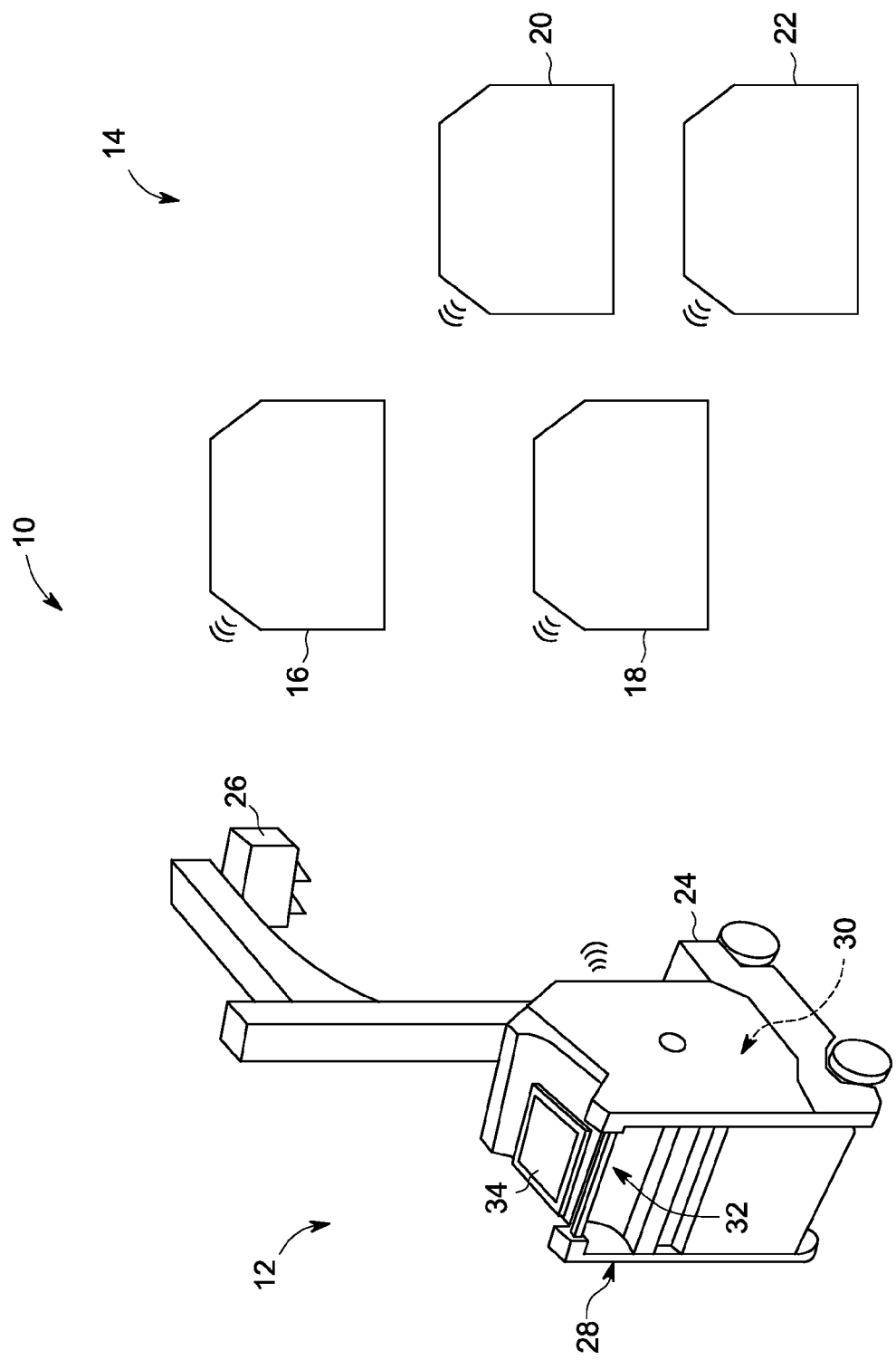
FIG. 1 is a perspective view of a wireless X-ray system, in accordance with aspects of the present technique.

Referring generally to FIG. 1, a wireless X-ray system is represented, referenced generally by reference numeral 10. In the illustrated embodiment, the wireless X-ray system 10 is a digital X-ray system designed both to acquire original image data and to process the image data for display in accordance with the present techniques. In the embodiment illustrated in FIG. 1, the wireless X-ray system 10 includes an X-ray base station 12 in wireless communication with multiple digital X-ray detectors 14, 16, 18, 20, and 22 located within the operative range of the X-ray base station 12. The X-ray system 10 is configured to coordinate operation of the multiple digital X-ray detectors 14. The X-ray base station 12 may be a mobile imaging system that includes a wheeled base 24. Alternatively, the X-ray base station 12 may be a fixed imaging system. The X-ray base station 12 has an X-ray source 26 and in conjunction with the digital X-ray detector 14 is operable to perform X-ray imaging. The X-ray base station 12 may recognize and communicate with the multiple X-ray detectors 14, as previously described in U.S. patent application Ser. No. 11/934,338 filed on Nov. 2, 2007, and U.S. patent application Ser. No. 12/506,067 filed on Jul. 20, 2009, which are hereby incorporated by reference.

The multiple X-ray detectors 14 may have one of a variety of statuses in relation to the wireless X-ray system 10 including an active status where the detector 14 is the desired recipient of radiation during a current X-ray imaging sequence, an inactive status where the detector is not the desired recipient of radiation during a current X-ray imaging sequence, or an unenabled status where the detector is not configured to operate with the X-ray base station 12. For example, the detectors 14 may include among them an active detector 22, one or more inactive detectors 16 and 18, or an unenabled detector 20. Of course, the particular terms used for such designations may be different, and the terms "active", "inactive" and "unenabled" used in the present discussion are not intended to be limiting or to imply any particular functionality or lack thereof other than as described.

A patient may be located between the X-ray source 26 and one of the detectors 14. During an imaging sequence, the detector 14 receives X-rays that pass through the patient and transmits imaging data to a base unit 28. The multiple detectors 14 are in communication with a base unit 28. The base unit 28 houses systems electronic circuitry 30 that detects the detectors, acquires image data from the detectors, and processes the data to form desired images. In addition, the systems electronic circuitry 30 both provides and controls power to the X-ray source 26 and the wheeled base 24 (for mobile systems). The base unit 28 also has an operator workstation 32 that enables a user operate the wireless X-ray system 10. The recognized detectors 14 detected by the systems electronic circuitry 30 are displayed on a display 34.

FIG. 2 illustrates diagrammatically the wireless X-ray system 10 of FIG. 1. The X-ray base station 12 includes a source of X-ray radiation 26. The source 12 is controlled by a power supply 36 which furnishes both power and control signals for examination sequences. In addition, in mobile imaging systems the power supply 36 furnishes power to a mobile drive unit 38 of the wheeled base 24. The power supply 36 is responsive to signals from a system controller 40. In general, system controller 40 commands operation of the imaging system to execute examination protocols and to process acquired image data. In the present context, system controller 40 also includes signal processing circuitry, typically based upon a general purpose or application-specific digital computer, associated memory circuitry for storing programs and routines executed by the computer, as well as configuration parameters and image data, interface circuits, and so forth. The system controller 40 may include or may be responsive to a processor 42. The processor 42 receives image data from the detector 14 and processes the data to reconstruct an image of a subject.

Also, the processor 42 is linked to detection circuitry 44 for detecting the presence of detectors within the operative range of the X-ray base station 12. If no detector 14 is active within the operative range of the X-ray base station 12, the processor 42 may send a signal to the system controller 40 to disable or inhibit the emission of X-rays from the X-ray base station 12. The detection circuitry 44 is also linked to the system controller 40. The detection circuitry 44 is linked to a wireless communication interface 46 that allows wireless communication with the detectors within the operative range of the X-ray base station 12. Further, the detection circuitry 44 is linked to a wired communication interface 48 that allows communication with a detector 14 connected to the X-ray base station 12 via a tether (e.g., a multi-conductor cable). The X-ray base station 12 may also be in communication with a server. The processor 40 is also linked to a memory 50, an input device 52, and the display 34. The memory 50 stores detector identification data, configuration parameters, and calibration files received from multiple detectors 14. The input device 52 may include a mouse, keyboard, or any other device for receiving user input to select or associate detectors 14 for use with the X-ray system 10, as well as to acquire images using the X-ray base station 12. The display 36 allows visualization of output system parameters, images, lists of detectors 14 within operative range of the X-ray base station 12, statuses of detectors 14, and so forth.

The detector 14 includes a wireless communication interface 54 for wireless communication with the X-ray base station 12, as well as a wired communication interface 56, for communicating with the detector when it is tethered to the X-ray base station 12. The detector 14 may also be in communication with a server. It is noted that the wireless communication interface 54 may utilize any suitable wireless communication protocol, such as an ultra wideband (UWB) communication standard, a Bluetooth communication standard, or any 802.11 communication standard. Moreover, detector 14 is coupled to a detector controller 58 which coordinates the control of the various detector functions. For example, detector controller 58 may execute various signal processing and filtration functions, such as for initial adjustment of dynamic ranges, interleaving of digital image data, and so forth. The detector controller 58 is responsive to signals from the system controller 40, as well as the detection circuitry 44. The detector controller 58 is linked to a processor 60. The processor 60, the detector controller 58, and all of the circuitry receive power from a power supply 62. The power supply 62 may include a battery. Alternatively, the detector 14, including the power supply 62, may receive power from the power supply 36 when tethered to the X-ray base station 12.

Also, the processor 60 is linked to detector interface circuitry 64. The detector 14 converts X-ray photons received on its surface to lower energy photons. The detector 14 includes a detector array 66 that includes an array of photodetectors to convert the light photons to electrical signals. Alternatively, the detector 14 may convert the X-ray photons directly to electrical signals. These electrical signals are converted to digital values by the detector interface circuitry 64 which provides the values to the processor 60 to be converted to imaging data and sent to the X-ray base station 12 to reconstruct an image of the features within a subject. Alternatively, the imaging data may be sent from the detector 14 to a server to process the imaging data.

The processor 60 is also linked to an illumination circuit 68. The detector controller 58, in response to a signal received from the X-ray base station 12, may send a signal to the processor 60 to signal the illumination circuit 68 to illuminate a light to indicate the active status (or where desired, any status) of the detector 14 in response to the signal. Further, the processor is linked to a memory 70. The memory 70 may store various configuration parameters, calibration files, and detector identification data. The detector identification data may include a serial number, a MAC address, a name associated with the detector, or other identifier data (e.g., color or shape). In addition, the memory 70 may store a list of all the X-ray systems 10 with which the detector 14 is configured to operate, as well as a table that defines the compatibility of the detector 14 with specific versions of X-ray systems 10 and/or software versions.

In order for the wireless X-ray system 10 to coordinate the operation of the system 10 when multiple detectors 14 are within the operative range of the X-ray base station 12, as shown in FIG. 1, any detector 14 to be used with the X-ray base station 12 needs to be registered to enable the use of the detector 14 with the system 10. The routine for automatic configuration of the detector 14 may occur as previously described in U.S. patent application Ser. No. 11/164,438, filed Nov. 22, 2005, which is hereby incorporated by reference. FIG. 3 illustrates the X-ray base station 12 of FIG. 1 tethered to the detector 14 for configuration (or enabling) of the detector 14 for operation with the X-ray system 10. The detector 14 is connected to X-ray base station 12 via a cable or tether 72 in order to register the detector 14. In a presently contemplated embodiment, the detector 14 need only be tethered once to the X-ray base station 12 for registration with the X-ray system 10 (although it could be tethered when desired). Also, in some embodiments the registration may occur wirelessly. In embodiments utilizing wireless registration, the detectors 14 may include a button that may be pressed in response to instructions received from the X-ray base station 12 to select the detector 14 for registration, whereupon the selection may be confirmed via a blinking light or some other indicator. After registration, any upgrades (e.g., of the configuration data) or changes in the status of the detector 14 may occur wirelessly. Upon connecting the detector 14 to the X-ray base station 12 during registration, the wireless communication (e.g., via UWB) between the connected detector 14, as well as the other detectors 14 within operative range, and the X-ray system 10 is disabled. The wireless X-ray system 10 transfers system identification data to the detector 14. The detector 14 transfers to the X-ray system 10 calibration files and operation parameters, such as the initial bad pixel maps and a gain map, as well as the firmware and software versions used by the detector 14 during registration. The X-ray system 10 verifies the detector firmware and software versions with the system 10. If the firmware or software is incompatible or out of date, then the system 10 updates the firmware or software on the detector 14. The detector 14 also transfers detector identification data, such as a serial number for the detector 14, to the system 10 during registration. The X-ray system 10 may also receive a list of other systems 10 registered with the detector 14. Each detector 14 may have a limited capacity as to the number of systems 10 associated with the detector 14. The X-ray system 10 may offer the user the capacity to manage the list of systems 10 registered or associated with the detector 14. The detector 14 and systems 10 may also be associated as described in U.S. patent application Ser. No. 12/776,166, entitled "SYSTEM AND METHOD FOR INDICATING ASSOCIATION BETWEEN AUTONOMOUS DETECTOR AND IMAGING SUBSYSTEM" filed on May 7, 2010, which is hereby incorporated by reference.

Upon connecting the detector 14 with the X-ray base station 12 via the tether 72, the user may register and assign a status to detector 14 relative to the X-ray system 10 via the operator workstation 32. FIG. 4 illustrates an example of a screen 74 shown on the display 34 of the X-ray base station 12 during the registration of the detector 14. The screen 74 represents only one example of what the screen 74 may look like and different versions of the screen 74 may be employed by one of ordinary skill in the art to register the detector 14. As illustrated, the screen 74 includes serial number indicator 76 of the detector 14 being registered. As mentioned above, the serial number is automatically provided to the X-ray system 10. The screen 74 also includes an option 77 to select an identification type to be registered. The available identification type selections include an option 79 to select a name or an option 81 to select a color and shape for registration. Upon selecting the identification type, a field 78 for the user to input a name or identifier data (e.g., color and shape) for the detector 14 appears. The screen 74 illustrates field 78 for the detector name. Alternatively, the field 78 may be for identifier data. If the name or identifier of the detector 14 inputted is already in use by another detector 14, the user is notified by the system 10 in order to input a different name.

To further help in the identification of the detectors 14, one or more identification mechanisms may be employed physically on the detector 14 and used in conjunction with the registration of the detector 14 with the system 10. For example, the detector 14 may be identified with a shape (e.g., circle, rectangle, triangle, etc.) and the shape may be color coded (e.g., blue, purple, yellow, etc.) to help further identify the detector 14. Additionally, the detector 14 may include rings that snap on to a handle of the detector 14 to help identify the detector 14. The rings may be color-coded or have other identifying data attached to them. Further, programmable electronic displays may be embedded in the detectors 14. These electronic displays may be programmed with a name, number, or symbol for the identification of the detector.

The screen 74 also includes an option 80 to assign the detector 14 an active status corresponding to a designation of the X-ray detector 14 as a desired recipient of radiation during a current X-ray imaging sequence. If the user does not assign the detector 14 the active status, then by default the detector 14 is assigned inactive status. However, in some embodiments, the screen 74 may include an option to assign the detector 14 an inactive status corresponding to a designation of the X-ray detector 14 as not the desired recipient of radiation during a current X-ray imaging sequence. Following registration, the detector need not be registered again with the X-ray system 10. Also, any subsequent updates of the detector 14 may be communicated wirelessly.

Figure 5:
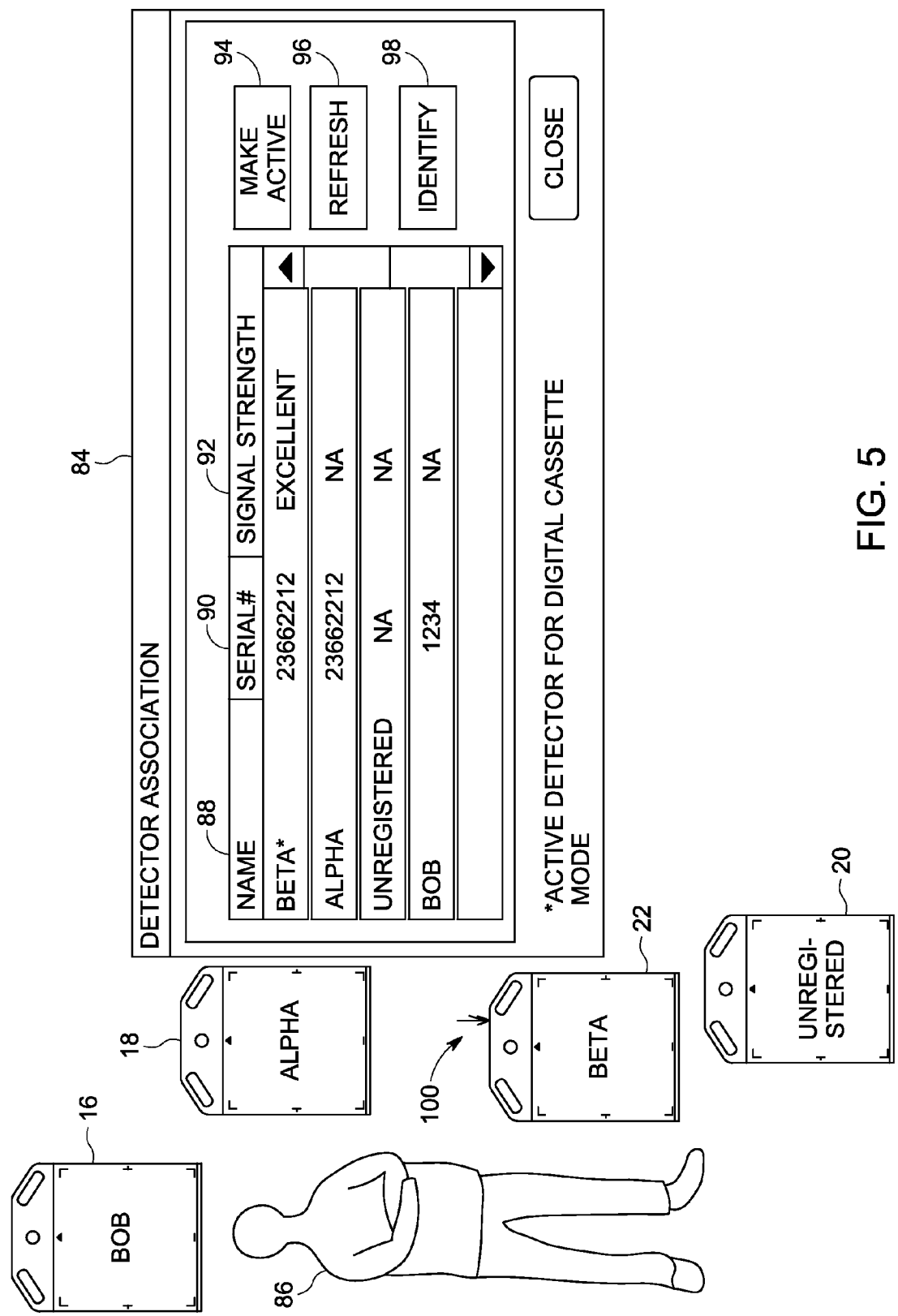
FIG. 5 is an example of a screen for displaying the statuses of detectors within the vicinity of the wireless X-ray system.

Besides registering detectors 14 in the coordination of multiple detectors 14, the X-ray system 10 recognizes the status of each detector 14 within the operative range of the X-ray base station 12 and provides a user-viewable screen to view the statuses of each detector 14, as well as to change the status of each detector 14. FIG. 5 illustrates an example of a user-viewable screen 84 shown on the display 34 of the X-ray base station 12 when multiple detectors are in the operative range of the X-ray base station 12 for use by a user 86. This screen 84 may appear either during the booting up of the X-ray system 10, a return of the system 10 from standby, or during imaging acquisition mode. The screen 84 may also be brought up by the user from other screens. As FIG. 5 illustrates the presence of active detector 22 (Beta), inactive detectors 16 and 18 (Bob and Alpha, respectively), and unregistered or unenabled detector 20. The user-viewable screen 84 lists all of the detectors 14 powered on within the operative range of the X-ray base station 12. The screen 84 includes a name 88 assigned for each detector 14. If the status of the detector 14 is unenabled (e.g., unregistered detector 20), the name 88 of detector 20 may be displayed as unregistered. A serial number 90 of each detector 14 and a signal strength 92 of the currently active detector 22 are also included on the screen 84. In the illustrated implementation, the signal strength 92 is only available for the active detector 22. Also, the serial numbers 90 are only listed for registered or enabled detectors 16, 18. The screen 84 lists the active detector 22 at the top and may provide an additional indication of the active detector 22, such as an asterisk. In the absence of an active detector 22, the X-ray base station 12 is disabled or inhibited from emitting X-rays.

The screen 84 also provides multiple options to the user 86 to coordinate the operation of the detectors 14 within the operative range of the X-ray base station 12. The screen 84 provides the user 86 the ability to select from among the registered detectors (16, 18, or 22) via the input device 52 located at the operator workstation 32. Then, the user may select a button 94 from screen 84 to make the selected detector 14 active. The user is also provided on screen 84 the option of selecting a button 96 to refresh the list to show the current status of each detector 14 within operative range. In some embodiments, the button 96 may be absent and the list may automatically refresh. A third option is provided to the user to identify among the detectors 14 the active detector 22. The user 86 may select a button 98 on the screen 84 to identify the active detector 22 via the input device 52. Upon selection of the identification button 98, the active detector 22 emits a user-discernible indication to identify the detector 22 as active. For example, the active detector 22 may have an LED that illuminates a light 100. The LED may blink repeatedly for a predetermined time (e.g., 10 seconds). Alternatively, the user-discernable indication may include an audible tone or a combination of the audible tone and light 100. The option of identifying the active detector 22 may only be available to the user 86 if the active detector 22 is selected from the list.

Figure 6:
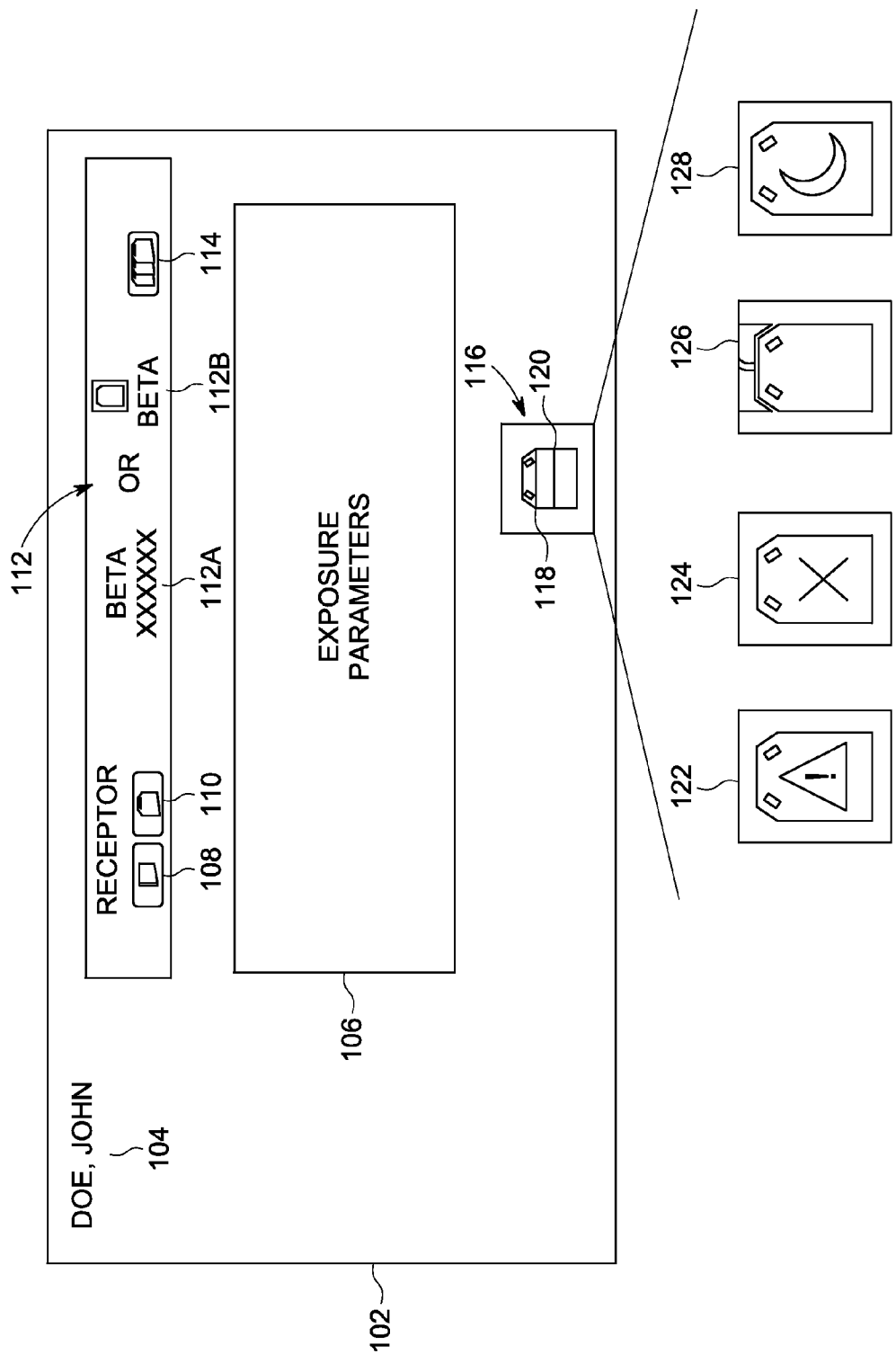
FIG. 6 is an example of a screen for displaying the acquisition status of the wireless X-ray system.

During acquisition of image data with an X-ray system 10, the system 10 includes additional features to coordinate the operation of detectors 14 within operative range. FIG. 6 illustrates a user-viewable screen 102 that may be shown on the display 34 of the X-ray base station 12. The user-viewable screen 102 includes patient identification information 104 (e.g., patient's name), as well as settings for exposure parameters 106 of the system 10. The screen 102 also provides the user the ability to select the desired mode for acquisition of images. The following modes represent only a few examples of modes available. The modes available may vary depending on the type of imaging system used. For example, a fixed imaging system may have a mode to select a detector 14 associated with a wall stand. The selection of icon 108 on screen 102 allows the user to acquire images using a film cassette. Alternatively, the selection of icon 110 allows the user to acquire images using digital X-ray detectors 14. In the digital detector mode, the screen 102 includes an indicator 112 identifying the active detector 22. In some embodiments, the indicator 112A includes the registered detector name and serial number of the detector 14. In other embodiments, the indicator 112B includes the registered detector name and an icon of a detector 14. If other detectors 14, besides the active detector 22, are identified within the operative range of the X-ray base station 12, individual icons for each detector 14 may appear on the screen 102 in some embodiments. These icons may include the name of the detector or other identifying data. Also, if multiple detectors are identified, a multiple detector icon 114 appears indicating that multiple detectors 14 are present. Selection of the multiple detector icon 114 allows the user to view the screen 84 of FIG. 5 listing all of the identified detectors 14. In some embodiments, the screen 102 may include icons for each available detector 14 to allow the user to select from the icons and to activate the desired detector 14.

The screen 102 further includes a detector status icon 116 that informs the user of the current status of the active detector 22, the absence of enabled detectors 14 within operative range, or if a detector 14 is connected to the system 10. The status icon 116 may appear on all of the user-interface screens. The detector status icon 116 at the bottom of the screen 102 in FIG. 6 illustrates an active detector battery status icon 118. The active battery status icon 118 indicates the available power left within the battery of the active detector 22 via a visual means (e.g., a line 120 or some other indicator) that indicates the power level of the battery. The detector status icon 116 may display other icons. For example, icon 122 indicates the absence of the active detector 22 operative range of the X-ray base station 12. When no detectors 14 are identified by the X-ray system 10, then the detector status icon 116 displays a detector icon 124 to indicate no detector 14 is available. As mentioned above, the absence of an active detector 22 results in the disabling or inhibition of the X-ray base station 12 from emitting X-rays while in the digital detector mode. A tethered detector icon 126 may also be available. The tethered detector icon 126 appears when detector 14 is tethered to the X-ray base station 12. When detector 14 is tethered, the indicator 112 indicates the identity of the tethered detector 14, even if the tethered detector 14 is not the active detector 22 associated with the X-ray system. Upon disconnecting the tether 72, the indicator 112 once again identifies the active detector 22. If the active detector 22 is in sleep mode, a detector sleep mode icon 128 appears. In order to wake up the active detector 22, the user must press the power on button of the active detector 22. Other detector status icons 116 may be included to represent additional states of the active detector 22 (e.g., docking of the active detector 22).

Figure 7:
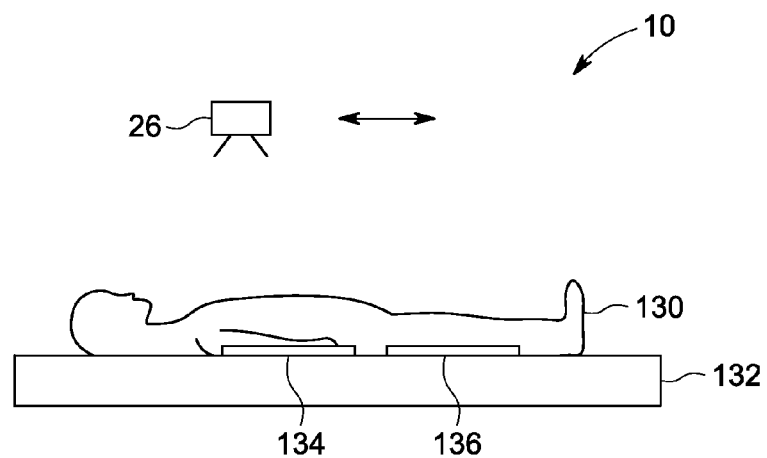
FIG. 7 is a diagrammatical side view of the use of multiple detectors, such as in a trauma situation.

The ability of the X-ray system 10 to coordinate multiple detectors 14 may be useful to the user under special circumstances, such as trauma situations. In such situations, medical personnel may prefer to move the injured person as little as possible. The ability to switch between multiple detectors 14 for imaging may reduce the need to move the injured person. FIG. 7 illustrates the use of multiple detectors 14 in such situations. FIG. 7 includes an X-ray system 10 that includes a patient 130 placed on a table 132 underneath the X-ray source 26. The system 10 also includes two enabled detectors 134 and 136 underneath the patient 132. Use of the detector coordination system, described above in FIGS. 5 and 6, allows a user to make either detector 134 or 136 active and a desired recipient of radiation during an X-ray imaging sequence of a first portion of the patient's anatomy. Following this X-ray imaging sequence, the source 26 may be moved and the other detector 134 or 136 not active in imaging the first portion of the patient's anatomy may be made active to be a desired recipient of radiation during a subsequent imaging sequence of a second portion of the patient's anatomy. The selection of either detector 134 or 136 as active makes the other detector 134 or 136 inactive.

Figure 8:
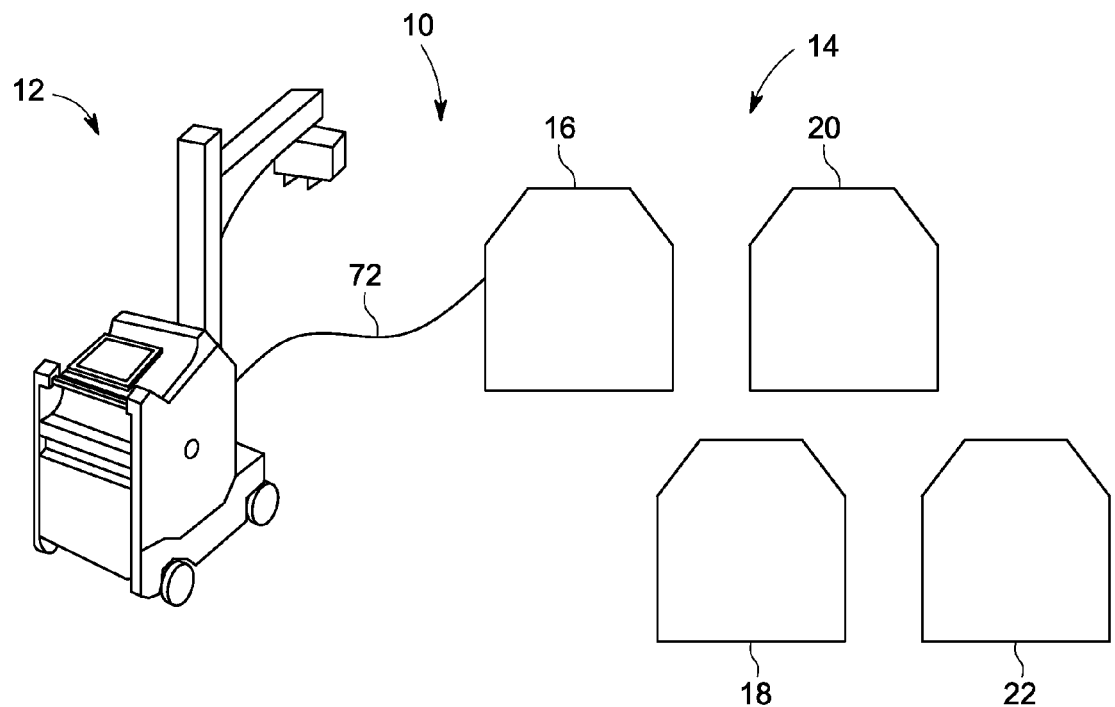
FIG. 8 is a perspective view of the wireless X-ray system of FIG. 1 with detector connected to an X-ray base station in the presence of multiple detectors.

Multiple scenarios may occur during the coordination of multiple X-ray detectors 14. For example, as briefly mentioned above, a detector may be tethered to the X-ray base station 12 in the presence of other detectors. FIG. 8 illustrates the wireless X-ray system 10 that includes multiple detectors 14, 16, 18, 20, and 22 located within the operative range of the X-ray base station 12. Detector 16 is coupled to the X-ray base station 12 via tether 72. If the X-ray system 10 is in acquisition mode to acquire an image of a subject, the tethered detector 16 may be used in acquiring the image data regardless of the status of the detector 14 relative to the system (active, inactive, unregistered). In addition, as mentioned above, when the tethered detector 16 is connected the wireless communication is disabled between the detectors 16, 18, 20, and 22 with the X-ray system 10. As described in FIG. 6, the tethered detector icon 126 appears on the display 34. If the user connects detector 16 after the start of the acquisition mode and activating one of the available detectors 18, 20, or 22, the system 10 generates an error message for the user on the display 34 indicating the desired detector 18, 20, or 22 cannot be found. In addition, the tethered detector icon 126 appears on the display 34.

Figure 9:
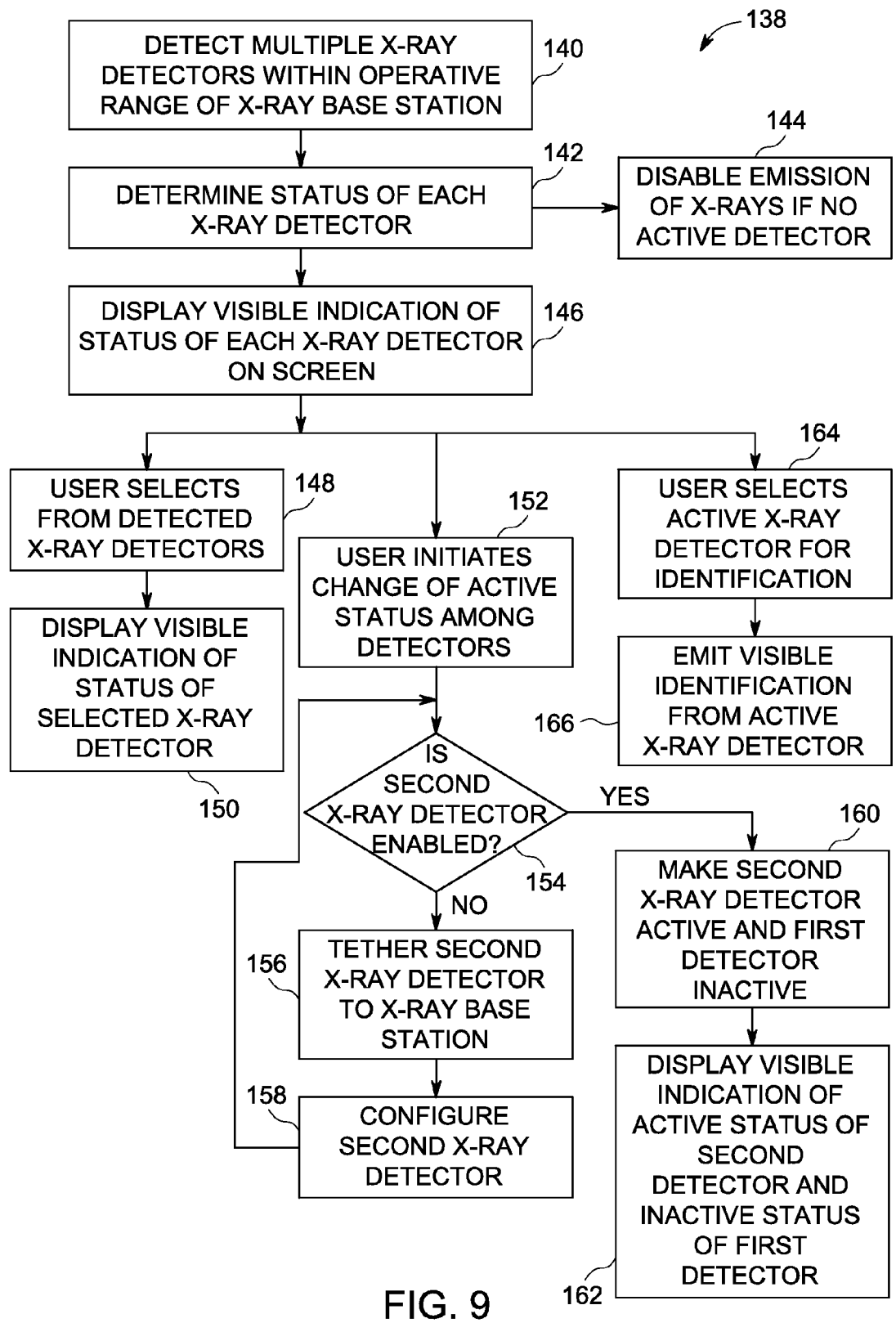
FIG. 9 is a flow diagram of a method for coordinating operation of X-ray detectors, in accordance with aspects of the present technique.

FIG. 9 illustrates a flow diagram of an exemplary method 138 for coordinating the operation of X-ray detectors 14. The method 138 includes detecting multiple X-ray detectors 14 within the operating range of the X-ray base station (block 140). As described above, only detectors 14 powered on are detected by the X-ray system 10. After detecting the multiple X-ray detectors 14, the system 10 determines the status of each X-ray detector 14 (block 142). The status of each detector 14 may be active, inactive, or disabled, as described above.

If no active detector 14 is registered with or detected by the system 10, then the emission of X-rays is disabled or inhibited (block 144) from the X-ray base station 12, if the system 10 is in digital detector mode. Upon determining the status of each detector 14, a visible indication of the status of each X-ray detector 14 is displayed on a user-viewable screen of the display 34 (block 146).

Multiple scenarios may occur after the display of each detector status. In one scenario, the user selects from the detected X-ray detectors 14 (block 148). Upon selection of one of the detectors 14, a visible indication of the status of the selected X-ray detector 14 is displayed (block 150). In another scenario, the user initiates a change in the active status among the detected detectors 14 (block 152). If a first detector 14 is already active, then a second detector 14 needs to be selected for active status by the user. In order to confer active status to the second detector 14, the system 10 makes a determination of whether the second detector 14 is enabled with the system 10 (block 154). If the second detector 14 is not enabled, then the second detector 14 is tethered to the X-ray base station 12 (block 156). After tethering, the second detector 14 is configured (block 158), as described above. If the second detector 14 is enabled, then the second detector 14 is made active and the first detector is made inactive (block 160). Following the change in status, a visible indication of the active status of the first detector 14 and the inactive status of the second detector 14 is displayed on a user-viewable screen of the display 32 (block 162). In a further scenario, the user selects a detector 14 with the active status for identification (block 164). In response to the user selection, the detector 14 with the active status emits a visible identification (block 166), such as the illumination of light from an LED described above. In alternative embodiments, the selection of the detector 14 for active status may occur differently. For example, the detector 14 may include a button or some other means that when pressed by the user makes the X-ray base station 12 aware that the detector 14 is the desired detector 14 for active status. In response to this indication, the X-ray base station 12 may recognize the detector 14 as the active detector 22.

The wireless X-ray detector coordination system described above allows the user to use the same detector 14 on multiple X-ray systems 10 during the hospital workflow. In addition, the coordination system allows the user to update the X-ray system 10 to use a new detector without the assistance of a field engineer. Further, the coordination system reduces the need for retakes by the user due to exposures occurring on the wrong detector 14 or if the calibration data of the detector 14 was not loaded on the X-ray system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for coordinating operation of X-ray detectors in a wireless X-ray system, comprising:
    detecting a plurality of wireless X-ray detectors within an operative range of an X-ray base station, a first of the X-ray detectors having an active status corresponding to a designation of the first X-ray detector as a desired recipient of radiation during a current X-ray imaging sequence, and a second X-ray detector having a status different from the active status;
    determining the current status of each detected X-ray detector; and
    displaying on a user-viewable screen a visual indication of the status of each detected X-ray detector.

2. The method of claim 1, wherein the second X-ray detector is configured to operate with the X-ray base station, and wherein the status displayed for the second X-ray detector is an inactive status corresponding to a designation of the second X-ray detector as not the desired recipient of radiation during a current X-ray imaging sequence.

3. The method of claim 2, comprising receiving a user input on the X-ray base station for changing which of the first and the second X-ray detectors has an active status.

4. The method of claim 1, wherein the second X-ray detector is not configured to operate with the X-ray base station, and wherein the status displayed for the second X-ray detector is an unenabled status.

5. The method of claim 4, comprising receiving a user input on the X-ray base station for configuring the second X-ray detector for operation with the X-ray base station.

6. The method of claim 5, wherein configuration of the second X-ray detector comprises an interchange of calibration data between the detector and the X-ray base station.

7. The method of claim 5, wherein configuration of the second X-ray detector comprises verifying compatibility of software and firmware of the detector for use with the X-ray base station.

8. The method of claim 1, comprising displaying on the user-viewable screen identifying data of the detected X-ray detectors.

9. The method of claim 1, comprising receiving a user input for indicating which of the first and second X-ray detectors has an active status, and emitting from the first X-ray detector a user-discernible indication that it has an active status.

10. The method of claim 9, wherein the user-discernible indication comprises illumination of a light from the first X-ray detector.

11. The method of claim 1, comprising displaying an icon on the user-viewable screen indicating that multiple X-ray detectors have been detected.

12. The method of claim 1, comprising displaying on the user-viewable screen a listing of all detected X-ray detectors within the operative range, receiving a user selection of one of the detected X-ray detectors, and displaying on the user-viewable screen a visual indication of the status of the selected X-ray detector.

13. A method for coordinating operation of X-ray detectors in a wireless X-ray system, comprising:
    detecting a plurality of wireless X-ray detectors within an operative range of an X-ray base station, the detected X-ray detectors each having one of multiple possible statuses, including an active status corresponding to a designation of the X-ray detector as a desired recipient of radiation during a current X-ray imaging sequence, an inactive status corresponding to a designation of the X-ray detector as not the desired recipient of radiation during a current X-ray imaging sequence, and an unenabled status corresponding to the X-ray detector not being configured to operate with the X-ray base station;
    determining the current status of each detected X-ray detector; and
    displaying on a user-viewable screen a visual indication of the status of each detected X-ray detector.

14. The method of claim 13, wherein the visual indication comprises a listing of the detected X-ray detectors and their respective status.

15. The method of claim 13, comprising disabling emission of X-rays from the X-ray base station if no detected detector has an active status.

16. The method of claim 13, comprising receiving a user input on the X-ray base station for changing which of the detected X-ray detectors has an active status, and changing the status of the X-ray detectors based upon the input.

17. The method of claim 13, comprising receiving a user input on the X-ray base station for configuring an X-ray detector having an unenabled status, and entering into a configuration routine in response to the input.

18. The method of claim 13, comprising receiving a user input for indicating which of the detected X-ray detectors has an active status, and emitting from the X-ray detector a user-discernable indication that it has an active status.

19. The method of claim 18, wherein the user-discernable indication comprises illumination of a light from the active X-ray detector.

20. The method of claim 13, comprising displaying an icon on the user-viewable screen indicating that multiple X-ray detectors have been detected.

21. The method of claim 13, comprising displaying on the user-viewable screen a listing of all detected X-ray detectors within the operative range, receiving a user selection of one of the detected X-ray detectors, and displaying on the user-viewable screen a visual indication of the status of the selected X-ray detector.

22. The method of claim 13, comprising receiving a user input identifying which X-ray detector is to have an active status.

23. The method of claim 22, wherein the user input originates from the X-ray detector that is to have the active status.

24. The method of claim 17, comprising wirelessly updating configuration data between the detector and the X-ray base station.

25. The method of claim 13, comprising assigning active status to any detector physically coupled to the X-ray base station.

26. A wireless X-ray detector operation coordination system, comprising:
   detection circuitry configured to detect a plurality of wireless X-ray detectors within an operative range of an X-ray base station and to determine a current status of each detected X-ray detector, the detected X-ray detectors each having one of multiple possible statuses, including an active status corresponding to a designation of the X-ray detector as a desired recipient of radiation during a current X-ray imaging sequence, an inactive status corresponding to a designation of the X-ray detector as not the desired recipient of radiation during a current X-ray imaging sequence, and an unenabled status corresponding to the X-ray detector not being configured to operate with the X-ray base station; and
   a user-viewable screen configured to display a visual indication of the status of each detected X-ray detector.

27. The system of claim 26, wherein the detection circuitry is provided in a fixed X-ray base station.

28. The system of claim 26, wherein the detection circuitry is provided in a mobile X-ray base station.

29. The system of claim 26, wherein the X-ray base station is configured to receive an input to change which of the detected X-ray detectors has an active status.

30. The system of claim 26, wherein the X-ray base station is configured to receive an input to configure an X-ray detector having an unenabled status and to enter into a configuration routine in response to the input.

31. The system of claim 26, wherein the X-ray base station is configured to receive an input to indicate which of the detected X-ray detectors has an active status, and the system comprises an active X-ray detector configured to emit a user-discernible indication in response to the input.

32. The system of claim 26, wherein the user-viewable screen is configured to display an icon indicating that multiple X-ray detectors have been detected.

\* \* \* \* \*